United States Patent
Mellin

[11] Patent Number: 6,102,851
[45] Date of Patent: Aug. 15, 2000

[54] LARYNGOSCOPE WITH REMOVABLE LIGHT SOURCE

[76] Inventor: Carl F. Mellin, 44 Hardwick St., Brighton, Mass. 02135

[21] Appl. No.: 09/276,037

[22] Filed: Mar. 25, 1999

[51] Int. Cl.[7] .................................................. A61B 1/267
[52] U.S. Cl. ......................... 600/199; 600/193; 600/198
[58] Field of Search .................................... 600/199, 200, 600/241, 245, 191, 223, 198, 197, 193

[56] References Cited

U.S. PATENT DOCUMENTS

| | | | |
|---|---|---|---|
| 1,686,041 | 10/1928 | Smith | 600/241 |
| 2,331,526 | 10/1943 | Wappler | 600/241 |
| 4,273,112 | 6/1981 | Heine et al. | 600/199 |
| 4,517,964 | 5/1985 | Upsher | 600/199 |
| 4,527,553 | 7/1985 | Upsher | 600/199 |
| 4,546,762 | 10/1985 | Upsher | 600/199 |
| 4,565,187 | 1/1986 | Soloway | 600/199 |
| 4,574,784 | 3/1986 | Soloway | 600/199 |
| 4,694,822 | 9/1987 | Bauman | 600/199 |
| 4,884,558 | 12/1989 | Gorski et al. | 600/199 |
| 5,060,633 | 10/1991 | Gibson | 600/199 |
| 5,529,570 | 6/1996 | Storz | 600/199 |

*Primary Examiner*—Paul J. Hirsch
*Attorney, Agent, or Firm*—Steven N. Fox; Hancock & Estabrook, LLP

[57] ABSTRACT

The present invention is a laryngoscope comprising a handle member having an upper portion and an internal cavity portion. The laryngoscope further comprises a blade member having a first end portion and a second end portion. The first end portion of the blade member is removably connected to the upper portion of the handle member. The laryngoscope further comprises a fiber optic cable having first and second ends extending from the first end portion of the blade member to substantially the second end portion of the blade member. The laryngoscope further comprises a light source removably disposed within the internal cavity of the handle member. The light source comprises a light emitting portion in communication with the first end of the fiber optic cable through the upper portion of the handle member to thereby transmit light through the fiber optic cable.

1 Claim, 3 Drawing Sheets

LARYNGOSCOPE WITH REMOVABLE LIGHT SOURCE

FIELD OF THE INVENTION

The present invention relates generally to laryngoscopes. More particularly, the present invention relates to laryngoscopes having a light source.

BACKGROUND OF THE INVENTION

It is well known to use a laryngoscope to insert an endotracheal tube through the mouth and throat and into the trachea of a patient. Such conventional laryngoscopes generally include a blade rotatably and removably attached to a handle. Blades are provided in a variety of sizes depending upon the size and contour of the patient's mouth and throat and any obstructions embedded therein. The blade has a channel which allows a medical professional to guide the endotracheal tube through the mouth and throat and into the trachea of a patient. To assist insertion of the endotracheal tube, conventional laryngoscopes have been provided with a means of directing light outward from the blade. Such light means typically include a non-removable light source formed within the handle which transmits a beam of light through a fiber optic cable disposed along the length of the blade and substantially adjacent the channel. The inability to remove the light source from the handle presents several drawbacks. After each use of the laryngoscope a sterilization process must be performed before the laryngoscope can be reused. Because of the material used in the manufacture of the blade and handle member of the laryngoscope, sterilization of laryngoscope can only be performed a finite number of times before the laryngoscope must be discarded. The cost of the light source is significantly greater than the cost of the handle and blade. As such, having to discard the laryngoscope along with the light source each time is the blade and/or handle must be discarded is a significant expense.

SUMMARY OF THE INVENTION

The primary object of the present invention is to provide a fully modular laryngoscope wherein the light source is removable from the handle thereby allowing the handle to be sterilized independent of the light source.

Another object of the present invention is to provide a fully module laryngoscope wherein the light source, handle, and optic fiber blade each constitute separate components, thereby allowing light source to be used for other diagnostic applications and to decrease the overall weight of the handle.

Another object of the present invention is to provide a laryngoscope which has a removable light source which when disposed within the handle can be turned on or off by the medical processional.

The present invention is a laryngoscope comprising a handle member having an upper portion and an internal cavity portion. The laryngoscope further comprises a blade member having a first end portion and a second end portion. The first end portion of the blade member is removably connected to the upper portion of the handle member. The laryngoscope further comprises a fiber optic cable having first and second ends extending from the first end portion of the blade member to substantially the second end portion of the blade member. The laryngoscope further comprises a light source removably disposed within the internal cavity of the handle member. The light source comprises a light emitting portion in communication with the first end of the fiber optic cable through the upper portion of the handle member to thereby transmit light through the fiber optic cable.

BRIEF DESCRIPTION OF THE DRAWINGS

The following description of the invention will be better understood with reference to the accompanying drawings in which.

DETAILED DESCRIPTION OF THE PREFERRED EMBODIMENTS

Figure 1:
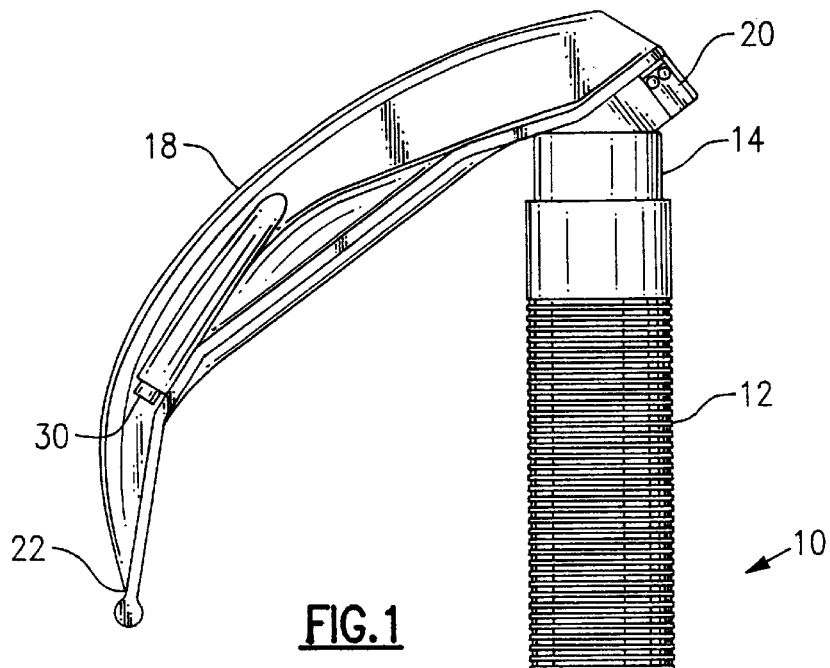
FIGS. 1 and 2 are perspective and assembled views of the laryngoscope of the present invention.
Figure 2:
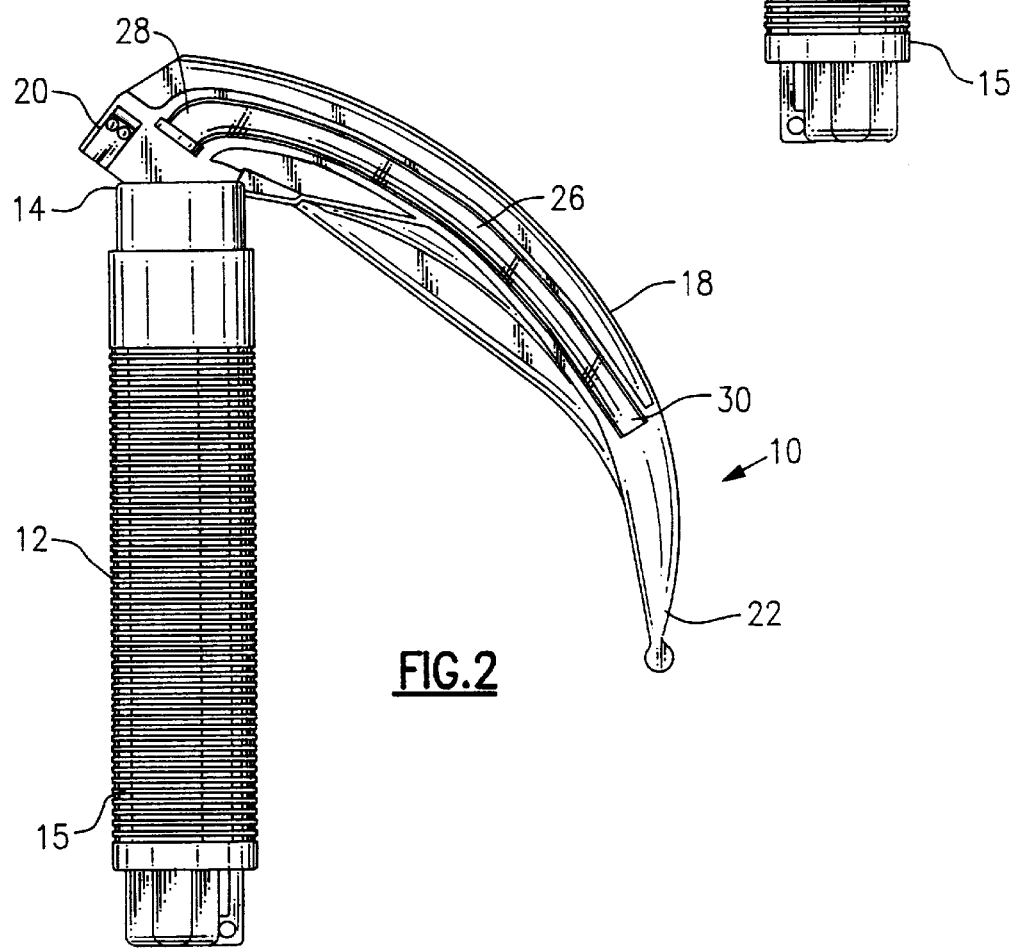
Figure 3:
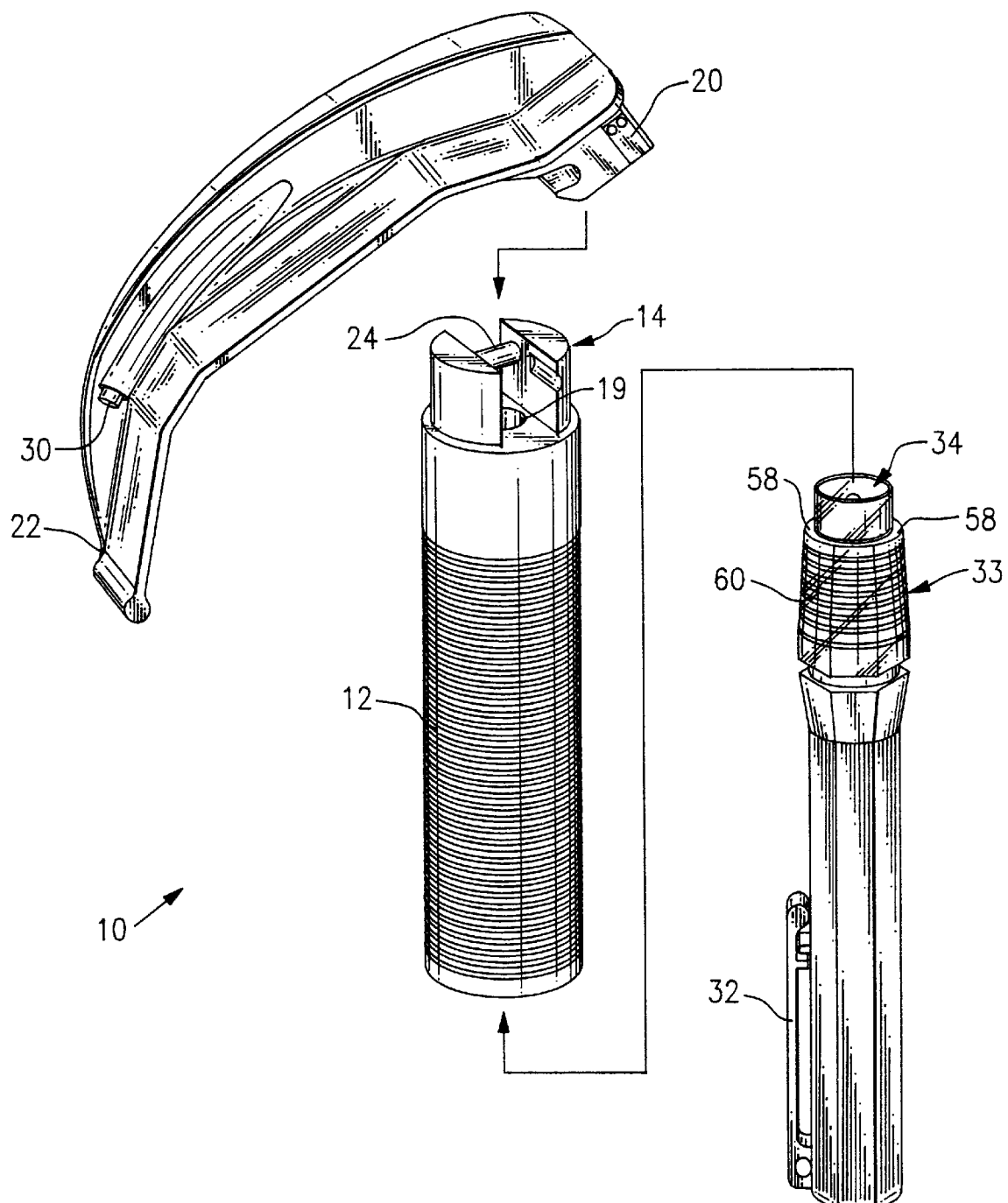
FIG. 3 is a perspective and exploded view of the laryngoscope of the present invention.
Figure 5:
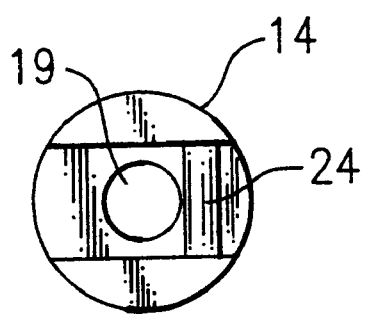
FIG. 5 is a top plan view of the handle member of the laryngoscope of the present invention.
Figure 4:
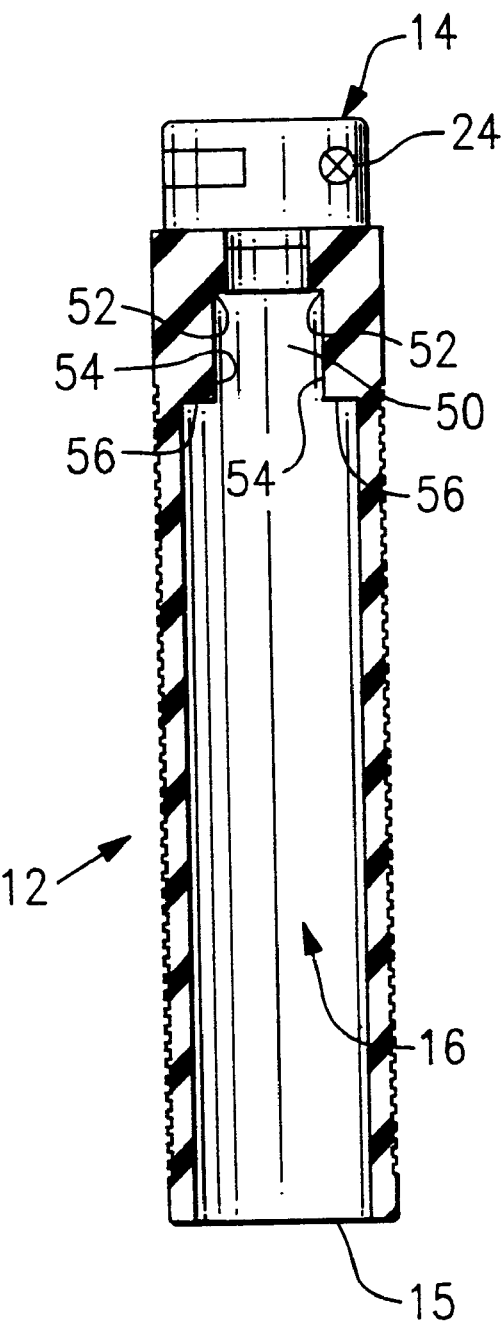
FIG. 4 is a cross-section view of the handle member of the laryngoscope of the present invention.

Referring to FIGS. 1–5, wherein the laryngoscope 10 of the present invention is generally shown comprising a handle member 12 having an upper end portion 14, a lower end portion 15, and an internal cavity portion 16. The internal cavity portion 16 comprises a lens 19 which functions to focus the light from the light source 32 (to be described) to the fiber optic cable 26 (to be described). The internal cavity portion 16 further comprises an upper cavity portion 50 having a shoulder portion 52 and side walls 56 and shoulders 54.

The laryngoscope 10 further comprises a blade member 18 having first and second end portions 20 and 22. The first end portion 20 of the blade member 18 is removably and rotatably connected to the upper portion 14 of the handle member 12 about a pin 24. The laryngoscope 10 further comprises a fiber optic cable 26 having first and second end portions 28 and 30 extending from the first end portion 20 of the blade member 16 to substantially the second end portion 22 of the blade member 16.

The laryngoscope 10 further comprises a light source 32 removably disposed within the internal cavity portion 16 of the handle 12. The light source 32 comprises an upper portion 33 having a light emitting portion 34 in communication with the first end portion 28 of the fiber optic cable 26 through the upper end portion 14 of the handle member 12. The upper portion 33 of the light source 32 further comprises a shoulder 58 and side walls 60. When the light source 32 is activated and inserted into the internal cavity portion 16 of the handle member 12, the shoulder 58 of the light source 32 abuts with the shoulder 52 of the handle member 12. Further, the sidewalls 60 of the light source 32 become frictionally engaged with the side walls 54 and shoulders 56 of the handle member 12. Upon complete insertion of the light source 32 within the cavity portion 16, the medical professional can rotate the light source 32 which causes the light source 32 and light emitting portion 34 to be turned on or off, and when on, causing the light to be transmitted through the lens 19 and to the fiber optic cable 20. The distance between the light emitting portion 34 of the light source 32 when inserted and the lens 19 is designed so as to provide a proper focal length to efficiently transmit light to the fiber optic cable 20. The distance between the light emitting portion 34 is in part controlled by the location of the shoulders 52 of upper cavity portion 50 relative to the position of the lens 19. The light source 32 may take a variety of forms and in the embodiment shown is a pocket light available from CFM Technologies, Inc., 192 Worcester Road, Wellesley Hills, Mass. 02481.

The foregoing description is intended primarily for purposes of illustration. This invention may be embodied in other forms or carried out in other ways without departing from the spirit or scope of the invention. Modifications and variations still falling within the spirit or the scope of the invention will be readily apparent to those of skill in the art.

What is claimed is:

1. A laryngoscope comprising:

a handle member having an upper portion and an internal cavity portion;

a blade member having first and second end portions, said first end portion being connected to said upper portion of said handle member;

a fiber optic cable having first and second ends disposed along said blade member; and;

a light source unit removably disposed within said internal cavity of said handle member, said light source unit comprising a housing having a light emitting upper portion, said light source unit further comprising a light source and a power supply contained within said housing and adapted to transmit a beam of light through said light emitting upper portion.

* * * * *